United States Patent [19]
Caporiccio et al.

[11] Patent Number: 4,731,170
[45] Date of Patent: Mar. 15, 1988

[54] PROCESS FOR PREPARING ALPHA, OMEGA-HALOPERFLUOROALKANES

[75] Inventors: Gerardo Caporiccio; Gianangelo Bargigia; Claudio Tonelli; Vito Tortelli, all of Milan, Italy

[73] Assignee: Ausimont S.p.A., Milan, Italy

[21] Appl. No.: 832,391

[22] Filed: Feb. 24, 1986

[30] Foreign Application Priority Data

Feb. 26, 1985 [IT]  Italy ................................ 19652 A/85

[51] Int. Cl.⁴ ..................... C07C 17/20; C07C 19/08; C07G 13/0
[52] U.S. Cl. ................ 204/157.95; 570/170
[58] Field of Search ............... 570/134, 137, 170; 204/158.11, 157.95

[56] References Cited

U.S. PATENT DOCUMENTS

| 2,788,375 | 4/1957 | Ehrenfeld | 204/157.95 |
| 3,016,407 | 1/1962 | Brace | 570/137 |
| 3,231,626 | 1/1966 | Hauptschein et al. | 570/170 |
| 3,337,435 | 8/1967 | Haszeldine | 570/139 |
| 3,371,123 | 2/1968 | Yale | 570/170 |
| 3,377,390 | 4/1968 | Rondestvedt | 570/137 |
| 3,377,392 | 4/1968 | Boudakian | 570/170 |
| 4,359,371 | 11/1982 | Bohm et al. | 570/134 |

FOREIGN PATENT DOCUMENTS 184033  9/1985  Japan ................................ 570/170

Primary Examiner—J. E. Evans
Attorney, Agent, or Firm—Stevens, Davis, Miller & Mosher

[57] ABSTRACT

A process for preparing $\alpha,\omega$-dihaloperfluoroalkanes consisting in dihalogenating $\alpha,\omega$-diiodoperfluoroalkanes, or $\alpha,\omega$-chloroiodoperfluoroalkanes or $\alpha,\omega$-bromoiodoperfluoroalkanes with $Cl_2$ or $Br_2$.

10 Claims, No Drawings

PROCESS FOR PREPARING ALPHA, OMEGA-HALOPERFLUOROALKANES

BACKGROUND OF THE INVENTION

This invention relates to a process for halogenating with $Cl_2$ or $Br_2$ telomers of tetrafluoroethylene characterized in that they have, at one end of their chain, a iodine end group, the other end group being selected from chlorine, bromine or iodine, and in which the products obtained consist of $C_2F_4$ units repeated n times, in which n varies from 2 to 6, extremes included, and the end groups of the chain are equal or different from each other and are selected from chlorine or bromine.

Known in the art and industrially produced are haloperfluoroalkanes, which are utilized in many technological fields depending on their chemical and chemical-physical characteristics.

A limitation to the use thereof is caused by their low boiling point, as is apparent from the following Table.

| Chemical formula | Boiling point (°C. at 1 at. abs.) | Examples of fields of use |
|---|---|---|
| $CCl_3F$ | +23.8 | Aerosol, foaming of polyurethanes |
| $CCl_2F_2$ | −29.8 | Aerosol, refrigeration, foaming of polyolefins |
| $CHClF_2$ | −40.8 | Refrigeration |
| $C_2Cl_3F_3$ | +47.6 | Solvent, foaming of resins |
| $C_2Cl_2F_4$ | +3.6 | Aerosol, foaming of polyolefins |
| $C_2ClF_5$ | −39.1 | Refrigeration |
| $CBrF_3$ | −57.8 | Flame extinguishing agent |
| $C_2Br_2F_4$ | +46.7 | Flame extinguishing agent |

These products, therefore, are utilizable only in fields where no high boiling points are required.

The synthesis methods known so far for preparing products exhibiting a higher molecular weight and by consequence a higher boiling point, having general formula $Cl(C_2F_4)_nCl$ with n $\geq 2$, are little selective or unsuited for a commercial-scale utilization.

For example in U.S. Pat. No. 3,381,043 it is stated that the addition reaction of chlorine to $C_2F_4$ is too strong as to be capable of giving rise to telomerization. In practice that means that the reaction stops at the first group $ClC_2F_4Cl$ and does not permit to introduce further units $C_2F_4$ between the two chlorine atoms in order to obtain the higher homologous products.

The above cited patent describes a process for preparing by telomerization the groups higher than $ClC_2F_4Cl$ by operating in the presence of $PCl_5$. However, the reaction with $PCl_5$, owing to the fact that this product is solid, requires the presence of solvents to promote a higher contact between the reagents. Generally, $CCl_4$ is used as a solvent.

In this case, however, the degree of utilization of the systems employed for the synthesis results to be reduced, with consequent considerable increase in the production costs.

Furthermore, according to said patent, the obtained products can be separated only by using gaschromatographic techniques. In fact, a fractioned distillation appears impossible for products $Cl(C_2F_4)_nCl$ wherein $n \leq 4$ because of the formation of azeotropes between $Cl(C_2F_4)_3Cl$ and $CCl_4$ employed as a solvent.

Only the fractions having $n > 4$ can be obtained by means of the distillation technique.

However, the products with $n \leq 4$ are the most interesting from a practical viewpoint.

This process for the preparation of telomers is of no practical interest from an industrial aspect because it is not proposable to use gaschromatographic techniques for preparing considerable amounts of the individual telomers with $n \leq 4$.

THE PRESENT INVENTION

It has now surprisingly been found that it is possible to prepare the products mentioned hereinabove, without operating in the presence of $PCl_5$ or of solvents, by means of the process forming the object of the present invention, by using, as a telogen, a derivative of $C_2F_4$ having, as end groups, at least a iodine atom, the other valence being saturated by a halogen atom of any kind, provided it is different from fluorine.

In fact it has been found that if $C_2F_4$ has both valences saturated with Br, the telomerization occurs with great difficulties, wherefore the yields of telomers are extremely low.

Thus, the present invention relates to a process for preparing tetrafluoroethylene telomers having general formula:

$$X(C_2F_4)_nY$$

wherein n is an integer ranging from 2 to 6, extremes included, preferably ranging from 2 to 4, and X and Y, either like or unlike each other, are Cl or Br. The process comprises the steps of preparing a tetrafluoroethylene telomer having an end group containing iodine, the other end group of the chain containing a halogen such as Cl, Br or I, and of subsequently reacting with $Cl_2$ or with $Br_2$.

The products obtainable according to the present invention are stabler than analogous products, preparable for example by addition of halogen (Cl or Br) to an olefinic double bond, because the latter have the halogen atoms bound to adjacent carbon atoms, that is in a favourable position for easily undergoing a dehalogenation with metals, for example zinc.

The process employed for preparing the products of the present invention consists in subjecting $C_2F_4$ to telomerization by using $Z-CF_2CF_2-I$ as a telogen according to the reaction:

$$Z-CF_2CF_2-I + (n-1) CF_2=CF_2 \rightarrow Z-(CF_2CF_2)_n-I$$

wherein Z is Cl, Br, I and n has the meaning indicated hereinabove,
and subsequent halogenation reaction with $Cl_2$ or $Br_2$ of $$Z-(CF_2CF_2)_n-I \text{ to yield } X-(CF_2CF_2)_n-Y$$

where n X and Y are the same as indicated hereinbefore.

The reaction according to the above scheme is carried out by telomerization of $C_2F_4$ using, as a telogen, 1,2-diiodotetrafluoroethane or 1-bromo-2-iodotetrafluoroethane or 1-chloro-2-iodotetrafluoroethane.

The latter are preparable in the pure state by reaction of iodine, iodine bromides of iodine chlorides with $C_2F_4$, employing $C_2F_4$/halogenating agent molar ratios equal to or lower than 1. Subsequently, the telomerization with $C_2F_4$, as indicated hereinafter, is carried out.

According to an alternative method, telomers Z—(CF$_2$CF$_2$)$_n$—I are directly preparable by using an excess of C$_2$F$_4$ with respect to the iodine halides or to the iodine and by successively reacting the resulting telomers with Cl$_2$ or Br$_2$ to obtain the products of the invention.

The telomerization may be conducted by means of heat at temperatures generally ranging from 150° to 250° C., or in the presence of peroxides at temperatures of from 45° to 250° C. The utilizable peroxides include peroxydicarbonates, such as e.g. bis-(4-tert.-butylcyclohexyl)peroxydicarbonate or bis-(4-alkylcyclohexyl)-peroxydicarbonate, in which the alkyl contains from 2 to 8 carbon atoms. There are employable also redox systems such as for example Cu$^+$/ethanolamine, Cu$^+$/diethanolamine.

According to the present invention, the subsequent reaction for introducing chlorine or bromine atoms is effected by directly treating α,ω-diiodoperfluoroalkanes, α,ω-bromoiodoperfluoroalkanes and α,ω-chloroiodoperfluoroalkanes with 0.5 to 10 moles of elemental Cl$_2$ or Br$_2$ per atom of iodine, preferably from 1 to 5, at temperatures ranging from 50° to 180° C.

The reaction may be conducted at ambient pressure, or under an autogenous pressure, depending on the employed halogen amount, on the reactor dimensions and on the temperatures at which the reaction is conducted, generally up to 30 atm. or above; the presence of ultraviolet radiations promotes the reaction so as to make it possible to use lower temperatures, generally from 0° to 50° C.

Examples of products obtained according to the present invention are:

Cl—(CF$_2$CF$_2$)$_2$—Cl
Br—(CF$_2$CF$_2$)$_2$—Br
Cl—(CF$_2$CF$_2$)$_3$—Cl
Cl—(CF$_2$CF$_2$)$_3$—Br
Cl—(CF$_2$CF$_2$)$_4$—Cl

The advantages deriving from the process described hereinbefore consist in permitting to obtain a whole class of products through a simple reaction, easily reproduceable on an industrial scale, without the need of employing solvents.

The reaction does not provide by-products because the iodine or the iodine halides are easy to indefinitely recover and recycle.

The products prepared by the process conforming to this invention are stable to chemical agents and to heat and exhibit good dielectric properties, wherefore they can be used as coolants for electric and electronic devices, also under tension, and as operating fluids for Rankine cycles.

In addition to the cited properties, they possess also densities by far higher than 1, wherefore they can be used as dielectric fluids for submerged devices, such as e.g. submarine cables.

The following examples are given merely to illustrate and not to limit the present invention.

EXAMPLE 1

Into a stainless steel AISI autoclave having a capacity of 5 l, equipped with a magnetic stirrer, there were charged 450 g (0.99 moles) of 1,4-diiodooctafluorobutane I—(C$_2$F$_4$)$_2$—I obtained by telomerization of C$_2$F$_4$ with I—C$_2$F$_4$—I and subsequent fractionated distillation.

After having closed and deaerated the autoclave with nitrogen, 360 g (5.1 moles) of chlorine were introduced. It was heated to 150° C. during 10 hours under a continuous stirring. It was cooled down, chlorine in excess was removed and the resulting product was washed with an aqueous solution of sodium bisulphite in order to remove traces of oxidants such as e.g. I$_2$ or Cl$_2$. The organic layer was then separated, which amounted to 256 g.

The gaschromatographic (GC) analysis (column of 4 m; fluorinated neutral oils Chromosorb W; Hewlett-Packard integrator; 100° C.) revealed that the product was Cl(C$_2$F$_4$)$_2$Cl and that is was particularly pure, because by-products were present only in traces. Further two peaks with a higher retention time were observed, the second of which exhibited the same retention time as I—(C$_2$F$_4$)$_2$—I which had been utilized as a reagent.

The NMR($^{19}$F) analysis (by a Varian XL 200) revealed, in an integration ratio of 1:1, two chemical shifts (δCCl$_3$F) respectively at:

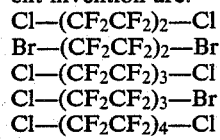

wherefore the product proved to have the following structure: ClCF$_2$CF$_2$CF$_2$CF$_2$Cl.

The main characteristics of the product were:

| | |
|---|---|
| boiling point | 65° C. |
| melting point | −83° C. |
| density | 1.65 g/cm$^3$ |
| latent heat of evaporation at boiling temperature | 7.5 kcal/mole |
| surface tension | 18 dynes/cm |
| vapour tension at 22° C. | 150 mm Hg. |

EXAMPLE 2

Into a cylindrical reactor (φ2 cm), made of glass, equipped with a fritted bottom for gas inlet, connected to an inert gas (N$_2$) line and to a chlorine cylinder and also equipped with two coolers connected in series and maintained at +15° C. and −40° C., respectively, 70 g (0.154 moles) of I(C$_2$F$_4$)$_2$I (prepared according to example 1) were introduced under a slight nitrogen flow.

The nitrogen flow was gradually substituted by a Cl$_2$ flow (0.5 l/h), and it was heated up to 140° C.; it was observed that the solution turned dark due to release of I$_2$ and that, as time passed, it tended to assume a straw yellow colour due to the forming of interhalogen compounds. At regular intervals of time samples were drawn for the GC analysis. After 8 hours 60% of the reagent was converted: for 8/10 to intermediate product Cl(CF$_2$CF$_2$CF$_2$CF$_2$)—I, boiling point: 107° C. (recognized through ($^{19}$F)NMR analysis: (δ, CFCl$_3$) at ppm 69; 119; 112; 59, respectively) and for the remaining 2/10 to final product Cl(C$_2$F$_4$)$_2$Cl. After further 8 hours, the conversion reached 85%, of which 45% to Cl(C$_2$F$_4$)$_2$I and 55% to Cl(C$_2$F$_4$)$_2$Cl.

By carrying out the reaction for additional 8 hours, a conversion of 95% to Cl(C$_2$F$_4$)$_2$Cl was obtained.

EXAMPLE 3

332 g (0.60 moles) of I(C$_2$F$_4$)$_3$I, prepared by telomerization, as indicated in example 1, and 230 g (3.2 moles) of chlorine were reacted in the same autoclave and according to the same modalities as described in example 1. It was heated to 150° C. during 10 hours.

Following the modalities described in example 1 there were isolated 205 g of a product which, on GC analysis, exhibited a peak at 6.4 min. corresponding to 98% of the total, the remaining 2% being recognized as consisting of I(C$_2$F$_4$)$_3$Cl and unreacted reagent I(C$_2$F$_4$)$_3$I. The ($^{19}$F) NMR analysis revealed that the product had the following chemical shifts ($\delta$, CCl$_3$F): Cl$\overline{CF_2}$ (ppm 69); ClCF$_2\overline{CF_2}$ (ppm 119); ClCF$_2$CF$_2\overline{CF_2}$ (ppm 121) corresponding to formula Cl(C$_2$F$_4$)$_3$Cl.

The product exhibited the following main characteristics:

| boiling point | 112° C. |
|---|---|
| melting point | −61° C. |
| density | 1.74 g/cm$^3$ |
| latent heat of evaporation at boiling temperature | 11 kcal/mole |
| surface tension | 21 dynes/cm |
| vapour tension at 20° C. | 18 mm Hg. |

EXAMPLE 4

The electrical characteristics of Cl(C$_2$F$_4$)$_2$Cl obtained in the test described in example 1 were evaluated.

By means of a Tettex 2821 apparatus with cell for fluids, the delectric constant and the dissipation factor (tg$\delta$) were determined.

As a function of potential difference $\Delta$V (at 50 Hz), the following results were obtained:

| $\Delta$V | dielectric constant (relating to air) | tg$\delta$ |
|---|---|---|
| 100 | 2.14 | 0.0043 |
| 500 | 2.14 | 0.0045 |
| 1000 | 2.14 | 0.0046 |
| 2000 | 2.14 | 0.0044 |

By means of a Hewlett Packard apparatus, type 4329A the volume resistivity was determined on the same fluid, in direct current; such resistivity, under a $\Delta$V of 1000 volts, being equal to 0.5·10$^{14}$.

EXAMPLE 5

87 g of I(C$_2$F$_4$)$_3$Cl (0.16 moles) were charged into an Inconel 250-ml autoclave. After having closed and de-aerated with N$_2$, 127 g (0.793 moles) of Br$_2$ were introduced. It was heated to 150° C. during 8 hours under continuous stirring. After cooling, it was washed, in the order, with water, 30% KOH, sodium bisulphite at 10%.

The organic layer (70 g) was separated. The GC analysis revealed a main peak (99%) and another peak equal to 1%, the retention time thereof being corresponding to the unreacted starting I(C$_2$F$_4$)$_3$I.

From the ($^{19}$F) NMR analysis obtained were three peaks of equal intensity ($\delta$, CCl$_3$F); BR$\overline{CF_2}$ (ppm 64); BrCF$_2\overline{CF_2}$(ppm 117); BrCF$_2$CF$_2\overline{CF_2}$(ppm 121), wherefore the product had the following formula:

BrCF$_2$CF$_2$CF$_2$CF$_2$CF$_2$CF$_2$Br.

EXAMPLE 6

Following the procedure described in example 2, 70 g (0.154 moles) of I(C$_2$F$_4$)$_2$I were reacted with chlorine during 8 hours.

The resulting product was rectified on an adiabatic column with automatic withdrawing.

25 g (0.06 moles) of the fraction corresponding to ClCF$_2$CF$_2$CF$_2$CF$_2$I were introduced into an AISI steel small autoclave along with 35 g of bromine (0.22 moles) and treated as is described in example 5.

On the basis of the ($^{19}$F) NMR analysis, the resulting product was recognized as ClCF$_2$CF$_2$CF$_2$CF$_2$Br. The chemical shifts were at: ppm 69 for Cl$\overline{CF_2}$; ppm 119 for ClCF$_2\overline{CF_2}$; ppm 117 for $\overline{CF_2}$CF$_2$Br; ppm 64 for $\overline{CF_2}$Br.

EXAMPLE 7

In order to evaluate the consistency of the $\alpha,\omega$-dichlorooctafluorobutane, obtained as is described in example 1, with plastomers and elastomers, rectangular weighed specimens of polymers were immerged during 72 hours in the abovesaid liquid maintained at 50° C.

The specimens were dried with filter paper and weighed again. The weight variations are indicated hereinbelow:

| polyethylene | +3.9% |
|---|---|
| polycarbonate | 0.0% |
| polysulphone | 0.0% |
| polyvinyl chloride | −0.1% |
| polymethylmethacrylate | −0.2% |
| polybutylene terephthalate | 0.0% |
| ABS | +0.3% |
| nylon 6 | −0.4% |
| polypropylene | +1.0% |
| butadiene-acrylonitrile copolymer | +1.0% |

From the obtained values it is inferable that the consistency of $\alpha,\omega$-dichlorooctafluorobutane with the polymers employed was excellent.

What is claimed is:

1. A process for preparing tetrafluoroethylene telomers of the formula X(C$_2$F$_4$)$_n$Y, wherein n is an integer from 2 to 6, and X and Y, the same or different, are Cl or Br, which comprises:
   (a) telomerizing tetrafluoroethylene with a telogen of the formula Z(C$_2$F$_4$)I, wherein Z is I, Br, or Cl, to form a telomer of the formula Z(C$_2$F$_4$)$_n$I, and
   (b) reacting Z(C$_2$F$_4$)$_n$I with chlorine or bromine at a temperature between 0° and 180° C. in the absence of solvent or diluent.

2. The process according to claim 1, wherein n is an integer from 2 to 4.

3. The process according to claim 1, wherein telomerization is effected at a temperature between 150° to 250° C.

4. The process according to claim 1, wherein telomerization is effected at a temperature between 45° and 250° in the presence of an organic peroxide.

5. The process according to claim 1, wherein Z(C$_2$F$_4$)$_n$I is reacted with from 0.5 to 10 moles of chlorine or bromine per atom of iodine.

6. The process according to claim 5, wherein Z(C$_2$F$_4$)$_n$I is reacted with from 1 to 5 moles of chlorine or bromine per atom of iodine.

7. The process according to claim 1, wherein the reaction of Z(C$_2$F$_4$)$_n$I with chlorine or bromine is effected at a temperature between 50° and 180° C.

8. The process according to claim 1, wherein the reaction of Z(C$_2$F$_4$)$_n$I with chlorine or bromine is effected at a temperature between 0° and 50° in the presence of UV radiation.

9. The process according to claim 1, wherein the reaction of Z(C$_2$F$_4$)$_n$I with chlorine or bromine is effected under the autogenous pressure of the chlorine or the bromine.

10. The process according to claim 1, wherein the reaction of Z(C$_2$F$_4$)$_n$I with chlorine or bromine is effected at ambient pressure.

* * * * *